United States Patent [19]

Takagi et al.

[11] Patent Number: 4,654,132

[45] Date of Patent: Mar. 31, 1987

[54] SEPARATION AND PURIFICATION OF BIOMEMBRANE PROTEINS

[75] Inventors: Toshio Takagi, Ibaraki; Masahiro Fukuda, Narashino; Kazuo Ohbu, Yokohama, all of Japan

[73] Assignee: Lion Corporation, Tokyo, Japan

[21] Appl. No.: 758,247

[22] Filed: Jul. 24, 1985

[30] Foreign Application Priority Data

Jul. 30, 1984 [JP] Japan .................................. 59-157643

[51] Int. Cl.⁴ ......................... B01D 57/02; C07K 3/14
[52] U.S. Cl. ................................................ 204/182.8
[58] Field of Search ......................... 204/299 R, 182.8

[56] References Cited

U.S. PATENT DOCUMENTS 4,481,094  11/1984  Fernandez de Castro et al. ..................................... 204/299 R

FOREIGN PATENT DOCUMENTS 137753  4/1985  European Pat. Off. ......... 204/182.8

OTHER PUBLICATIONS

*Kodak Products for Gel Electrophoresis,* Eastman Kodak Co., Rochester, New York, pp. 16-17, (Oct. 1985).
Biochimica et Biophysica Acta, 748, (1983), pp. 153-167, (Yutaro Hayashi et al).
Biochimica et Biophysica Acta, 356, (1974), pp. 36-52, (Peter Leth Jorgensen).
Recipient of American Cancer Society Faculty Award PRA-69, pp. 179-246, (Jacob V. Maizel, Jr.).

*Primary Examiner*—Howard S. Williams
*Attorney, Agent, or Firm*—Armstrong, Nikaido, Marmelstein & Kubovcik

[57] ABSTRACT

A method for separating and purifying a biomembrane protein from biomembrane by subjecting the biomembrane to gel electrophoresis in the presence of at least one anionic surfactant having the general formula (I):

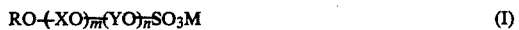

$$RO-(XO)_{\overline{m}}(YO)_{\overline{n}}SO_3M \quad (I)$$

wherein R represents an alkyl group having 6 to 22 carbon atoms or an alkylphenyl group having 6 to 22 carbon atoms, X and Y independently represent a hydrocarbon residue having 1 to 4 carbon atoms, m and n independently represent a number of from zero to 40 provided that m+n is 4 to 40, and M represents an alkali metal, an alkaline earth metal, an amine, or ammonium.

Thus, the desired biomembrane protein can be separated and purified with a high purity without denaturing the protein and also without impairing the biological function thereof.

5 Claims, No Drawings

SEPARATION AND PURIFICATION OF BIOMEMBRANE PROTEINS

BACKGROUND OF THE INVENTION

1. Field of the Invention

The present invention relates to a method for separating and purifying a biomembrane protein from a biomembrane. A biomembrane protein separated and purified at a high purity is important not only for studying the function and structure of a biomembrane protein, but also because it has become useful as a product in the fields of pharmacology, medicine, and engineering. According to the present invention, the desired biomembrane protein can be separated and purified from a biomembrane, with a high purity and without impairing the biological function thereof, by subjecting the biomembrane to gel electrophoresis in the presence of a specified anionic surfactant.

2. Description of the Related Art

A biomembrane is composed mainly of polar lipids and membrane proteins. The membrane proteins maintaining their biological functions are inserted into a bilayer membrane composed of the polar lipid, especially phospholipids.

Most of the biomembrane proteins such as porin of the *Escherichia coli* outer membrane, cytochrome $b_5$, $(Na^+, K^+)$ATPase, $(Ca^{++})$ATPase, and $(H^+)$ATPase are only slightly soluble in water and, therefore, when these proteins are separated from the biomembrane, the desired biomembrane protein should be solubilized in the first step of the separation and purification operation, unlike water-soluble globular proteins. To solubilize membrane proteins, media having an environment or situation similar to that of the lipid bilayer are required. Various organic solvents and surfactants have been used for the above-mentioned purpose. Typical examples of such organic solvents being acetone, butanol, ethanol, pyridine, and so on and typical examples of such surfactants being anionic surfactants represented by sodium dodecylsulfate, cationic surfactants represented by trimethyldodecyl ammonium chloride, and nonionic surfactants represented by polyoxyethylene dodecyl ether. However, since most organic solvents act as a strong denaturing agent against proteins, it is usually difficult to separate and purify the desired biomembrane protein from the biomembrane without impairing the biological function thereof. Furthermore, since sodium dodecylsulfate, (i.e., "SDS") conventionally used as a typical anionic surfactant in biochemical fields acts as a strong protein denaturing agent, it is usually difficult to separate and purify the desired biomembrane protein without impairing the biological function thereof. Various attempts have been made to solve the above-mentioned difficulties by using, as a medium for solubilizing biomembrane proteins, nonionic surfactants having a low protein denaturation power. However, the critical micelle concentrations of most nonionic surfactants are so low that it becomes difficult to remove the surfactant molecules bound to the protein by dialysis after the separation and purification of the desired biomembrane protein.

Bile acid salts may be used, as an anionic surfactant having a low protein denaturation power, for solubilizing biomembrane protein. However, the bile acid salts or similar natural surface active substances are practically useless in that they are not available in large amounts for commercial or industrial use. On the other hand, cationic surfactants are commonly used as a germicide, since they are strongly bound to lipids constituting the biomembrane when compared with the other surfactants, and since the denaturation power of cationic surfactants against protein is not weak. There are few (or substantially no) cases in which the separation and purification of the biomembrane proteins can be successfully carried out by using cationic surfactants. Thus, these cationic surfactants are not widely used in the separation of the biomembrane proteins.

Various separation and purification methods utilizing the physical or chemical characteristics of proteins have been proposed, such as thermal or pH treating methods, fractional precipitation methods, absorption and desorption methods, chromatographic methods utilizing ion exchanging, isoelectric fractionation methods, density gradient centrifugation methods, electrophoresis methods, affinity chromatographic methods, molecular sieve methods, two phase partition methods, and crystallization methods. These methods have both merits and demerits.

SUMMARY OF THE INVENTION

Accordingly, the objects of the present invention are to eliminate the above-mentioned disadvantages and to provide a method for separating and purifying a biomembrane protein from a biomembrane, by utilizing gel electrophoresis in the presence of a specified anionic surfactant, with a high purity and without causing any denaturation of the protein or impairing the biological function thereof.

Other objects and advantages of the present invention will be apparent from the description set forth hereinbelow.

In accordance with the present invention, there is provided a method for separating and purifying a biomembrane protein from a biomembrane by subjecting the biomembrane to gel electrophoresis in the presence of at least one anionic surfactant having the general formula (I):

$$RO-XO)_m (YO)_n SO_3M \qquad (I)$$

wherein R represents an alkyl group having 6 to 22 carbon atoms or an alkyl phenyl group having 6 to 22 carbon atoms, X and Y independently represent a hydrocarbon residue having 1 to 4 carbon atoms, m and n independently represent a number of from zero to 40 provided that m+n is 4 to 40, and M represents an alkali metal, an alkaline earth metal, an amine, or ammonium.

DESCRIPTION OF THE PREFERRED EMBODIMENTS

(1) Surfactants

The anionic surfactants usable in the present invention for solubilizing a biomembrane protein without denaturing the protein are those having the above-mentioned general formula (I). In the general formula (I), R represents an alkyl group having 6 to 22 carbon atoms or an alkylphenyl group having 6 to 22 carbon atoms. The alkyl group may be linear or branched and R may have unsaturated hydrocarbon atoms. X and Y independently represent a hydrocarbon residue having 1 to 4 carbon atoms such as $-CH_2-$, $-CH_2CH_2-$, $-CH_2CH(CH_3)-$, and $-CH_2CH(C_2H_5)-$ and these may be either a homopolymer, block copolymer, or random copolymer. The references m and n independently represent a number from zero to 40, provided that m+n is 4 to 40, which represent the addition mole number or the average addition mole number of aklylene oxides. M represents an alkali metal such as sodium, lithium, potassium, an alkaline metal such as magnesium, calcium, an amine such as triethanolamine, diethanolamine, monoethanolamine, monoisopropanolamine, diisopropanolamine, triisopropanolamine, pyridine, morpholine, or ammonium. When the carbon atom number of R in the formula (I) is less than 6, the biomembrane protein cannot be effectively solubilized due to a decrease in the surface activity of the surfactant. Contrary to this, when the carbon atom number of R in the formula (I) is more than 22, it becomes difficult to remove the surfactant molecules by dialysis from the membrane protein-surfactant complexes after the separation of the protein.

Preferably, group R is a linear alkyl group having 8 to 16 carbon atoms or a branched alkylphenyl group having 6 to 14 carbon atoms and m+n is 4 to 20. Especially, anionic surfactants having the general formula (I) in which R is a linear alkyl group having 10 to 14 carbon atoms or a branched alkylphenyl group having 8 to 12 carbon atoms, X and Y are $-CH_2CH_2-$, and m+n is 4 to 15. In the general formula (I), when m+n is 3 or less, the kinds of biomembrane proteins separated without impairing their biological functions are disadvantageously limited, since the denaturation power of the surfactant against the protein is increased. Contrary to this, when m+n is 21 or more, the surfactant exhibits nonionic surfactant-like phenomena in spite of being anionic surfactants and, therefore, it becomes difficult to remove the surfactant molecules by dialysis from the membrane protein-surfactant complexes after the separation of the desired biomembrane protein.

Examples of the anionic surfactants having the general formula (I) are as follows:

Polyoxyethylene (ave. 5 mol) octyl ether sulfates; polyoxyethylene (ave. 5 mol) decyl ether sulfates; polyoxyethylene (ave. 5 mol) lauryl ether sulfates; polyoxyethylene (ave. 8 mol) lauryl ether sulfates; polyoxyethylene (ave. 20 mol) lauryl ether sulfates; hexaoxyethylene dodecyl ether sulfates; octaoxyethylene dodecyl ether sulfates; poly (oxypropylene (ave. 2 mol)-oxyethylene (ave. 5 mol)) lauryl ether sulfates; poly (oxybutylene (ave. 1 mol)-oxyethylene (ave. 5 mol)) lauryl ether sulfates; polyoxyethylene (ave. 7 mol) cetyl ether sulfates; polyoxyethylene (ave. 10 mol) oleyl ether sulfates; polyoxyethylene (ave. 6 mol) sec-lauryl ether sulfates; polyoxyethylene (ave. 7 mol) octylphenyl ether sulfates; polyoxyethylene (ave. 7 mol) nonylphenyl ether sulfates; polyoxyethylene (ave. 12 mol) nonylphenyl ether sulfates.

Preferable examples of the anionic surfactants usable in the present invention are sodium polyoxyethylene (ave. 8 mol) lauryl ether sulfate, sodium octaoxyethylene dodecyl ether sulfate, sodium polyoxyethylene (ave. 6.9 mol) branched nonylphenyl ether sulfate, ammonium polyoxyethylene (ave. 7 mol) lauryl ether sulfate, triethanolammonium polyoxyethylene (ave. 6 mol) dodecyl ether sulfate, sodium poly (oxypropylene (ave. 2 mol)-oxyethylene (ave. 5 mol)) lauryl ether sulfate.

(2) Gel Electrophoresis

According to the present invention, the solubilized biomembrane protein is subjected to gel electrophoresis. The supporting media usable in the gel electrophoresis according to the present invention include, for example, cellulose acetate, Sephadex ® (Sepharose available from Pharmacia), vinyl chloridevinyl acetate copolymer, polyvinyl chloride, starch powder, starch gel, agarose gel, and polyacrylamide gel. Of these media, the use of polyacrylamide gel is especially preferable. This is because the polyacrylamide gel has various advantages; namely, it is chemically stable, the gel concentration and crosslink proportion can be freely controlled (i.e., the average pore size can be readily varied depending upon the intended use), it has substantially no electroendosmosis, it is not substantially affected by a change in the ambient pH and temperature, it can be formed or molded in any desired form or shape, and the reproducibility in the gel electrophoresis is very high.

A typical example of the electrophoresis operation according to the present invention will be now specifically explained. Although polyacrylamide gel is used as a supporting medium in the following explanation, it should be noted that the supporting medium usable in the present invention is by no means limited to polyacrylamide.

(i) Apparatus and Devices

These consist of a cylindrical tube supporting the polyacrylamide gel and vessels containing a buffers solutions provided at both sides of the tube. The dimensions and volumetric capacities of the cylindrical tube and vessels can be optionally decided or selected depending upon, for example, the kinds and amount of protein to be separated and purified.

(ii) Electric Power

The use of direct current generating apparatus, especially constant current or constant voltage generating apparatus, is preferable in that the capability and reproducibility of the method in the present invention is thereby increased, although any conventional electric power generation apparatus can be used in the practice of the present invention.

(iii) Preparation of Polyacrylamide Gel for Electrophoresis

A 1% to 30% by weight amount of acrylamide, 0.05% to 10% by weight, based on the amount of the acrylamide, of N,N'-methylene bisacrylamide, and 0.01% to 1% by weight of an anionic surfactant having the above-mentioned general formula (I) are dissolved in water. The resultant aqueous solution is polymerized to cause gelation. The preferable gel concentration is such that the total amount of the acrylamide and the N,N'-methylenebisacrylamide in the gel is 3% to 15% by weight, and the amount of the N,N'-methylenebisacrylamide is 1% to 5% by weight based on the amount of the acrylamide. Although there is no specific limitation to the concentration of the surfactant, the preferable concentration of the surfactant in the gel is 0.01 to 1% by weight, especially 0.05 to 0.2% by weight. It should be noted that any conventional additives such as polymerization catalysts, polymerization accelerators, pH buffers, and preservatives can be used in the gelation. For instance, photoinitiators such as riboflavin or radical polymerization initiators such as ammonium persulfate may be used in any conventional amount, preferably 0.04% to 0.12% by weight based on the weight of the polymerization mixture. Any conventional polymerization accelerators such as N,N,N',N'-tetramethyl ethylenediamine may also be used in any appropriate concentration, preferably 0.1% to 0.5% by weight.

Since the dissolved oxygen inhibits the gelation, it is sometimes preferable if the dissolved oxygen in the aqueous polymerization solution is degassed under reduce pressure and that the upper layer portion of the aqueous polymerization solution is overlayered with distilled water to prevent direct contact with air. The pH buffers optionally usable in the practice of the gelation include, for example, sodium dihydrogen phosphate-disodium hydrogen phosphate system, sodium carbonate-sodium hydrogen carbonate system. Thus the desired gel electrophoresis can be effected at an intended pH condition. Although there is no critical limitation to the concentration of the pH buffers, the concentration of the pH buffers is generally adjusted in the range of 10 to 500 mM, preferably 50 to 200 mM, more preferably about 100 mM.

(iv) Aqueous Solution in Buffer Vessels

Both ends of the polyacrylamide gel for the electrophoresis should be filled with a buffer solution. The buffer solution generally comprises a buffer which is used in the preparation of the aqueous solution, the surfactant, and water. The concentrations of the buffer and the surfactant are preferably the same as those used in the aqueous solution for the preparation of the above-mentioned polyacrylamide gel.

(v) Aqueous Solution Containing a Biomembrane Protein to be Separated

An aqueous solution containing biomembrane protein to be separated generally contains, in addition to the protein, 0.1% to 5% by weight, preferably 0.2% to 3% by weight, more preferably 0.5% to 2% by weight of the surfactant. This aqueous solution optionally contains 1% to 30% by weight, preferably 10% to 20% by weight, of viscous liquid such as glycerine to improve the desired separation and purification efficiency.

The above-mentioned aqueous solution may contain the buffer in the gel and the buffer solution. The concentration of the buffer in the aqueous solution is, preferably, 500 mM or less and is the same as or less than that of the above-mentioned buffer solution. The most preferable concentration of the buffer in the aqueous solution is ½ to 1/20 that of the above-mentioned buffer solution.

Furthermore, the above-mentioned aqueous solution may contain water-soluble anionic dyes such as bromphenol blue for showing the relative mobility, and micelle-soluble but water-insoluble coloring pigments or dyes such as oil-soluble Yellow OB dye for showing the mobility of the surfactant micelle. The concentration of these dyes and pigments can be appropriately selected but, preferably, the concentration of the water-soluble dyes is about 0.001% to 0.05% by weight and that of the water-insoluble pigments or dyes is 0.01% to 0.5% by weight.

The desired electrophoresis is started by placing the above-mentioned aqueous solution containing the biomembrane protein on the upper end portion of the polyacrylamide gel. The biomembrane protein is separated and purified in the form of a disc in the gel. After a dye staining is accomplished by immersing the gel in a dye solution, excess back ground stain is removed by repeated washing of the gel in 7% by weight acetic acid. The separated biomembrane protein in the form of a disc can be observed as a colored band. The dyes usable in this operation include, for example, amido black and Coomassie Brilliant Blue. The separation and purification of the designed biomembrane protein can be confirmed by any conventional method (e.g., see Katsuya Hayashi, "Experimental Method of Biochemistry-Electrical Properties of Protein" ed. by Ikuzo Uritani, Kensuke Shimura, Michinori Nakamura, and Katsuji Funazu, pages 30 to 39, published in 1971 by Gakkai Shuppan Center, Japan).

(3) Substance to be Separated and Purified According to the Present Invention The substances to be separated and purified according to the present method are all biomembrane proteins extracted and solubilized from, for example, animal organs, cultured cells, microorganism cells, and plant cells.

(4) Separation and Purification

Supernatant solutions containing all of the solubilized biomembrane protein can be directly separated and purified by the method according to the present invention. Furthermore, solutions containing the membrane proteins obtained by treatment of any conventional nucleic acid removal, or solutions obtained by previous treatment conventional initial purification methods according to with their intended purpose, such as fractional precipitation methods and density gradient centrifugation methods, can be further highly purified.

Note that, when the above-mentioned rough pretreatment is carried out prior to the practice of the separation and purification of biomembrane protein according to the present invention, it is preferable to use a method such that the biological function of the desired biomembrane protein is not impaired or that, even if the denaturing of the desired protein occurs, the desired activity can be reversibly recovered when factors causing the denaturation are eliminated. As mentioned above, the separation and purification method of a biomembrane protein according to the present invention can be advantageously applied to any kind of biomembrane proteins and to any separation and purification step of a biomembrane protein.

Although there are no critical limitations to the temperature and pH of the system during the separation and purification according to the present invention, the preferable temperature is 0° C. to 40° C., more preferably 0° C. to 20° C., and the preferable pH is 4 to 9, especially about 7. A temperature of less then 0° C. sometimes tends to allow the water in the gel to be frozen and, therefore, electrophoresis becomes impossible. Contrary to this, a temperature of more than 40° C. sometime tends to cause thermal denaturation of the desired biomembrane protein, whereby the biological function of the biomembrane protein is impaired. On the other hand, when the pH of the system is less than 4 or more than 9, an unpreferable acid or alkali denaturation of the protein sometimes occurs.

As mentioned hereinabove, according to the present invention, the following advantageous characteristic are obtained.

(a) The anionic surfactants having the general formula (I) have low protein denaturing properties and, unlike bile acid salts, they are readily synthesized industrially at a low cost.

(b) The protein denaturing properties of the anionic surfactants (I) are extremely low and similar to those of nonionic surfactants. Since the amount of the anionic surfactants (I) bound to the solubilized biomembrane proteins differs from one another, each protein-surfactant complex has a different electric charge. Therefore, these complexes move through electrophoresis supporting media at inherent velocities toward an anode. During this movement, molecular sieving effects of the supporting media can be utilized and, therefore, the separation and purification efficiency is extremely increased when compared with a conventional gel filtration method of a biomembrane protein solubilized with nonionic surfactants.

(c) The second defect of the conventional gel filtration methods of a biomembrane protein solubilized with nonionic surfactants is that the use of a large amount of a solvent is required. In the practice of the separation and purification method according to the present invention, the use of such a solvent is advantageously not required.

(d) It is often difficult to remove nonionic surfactants bound to a biomembrane protein by dialysis, because the critical micellar concentrations of nonionic surfactants are quite low. Contrary to this, since the critical micellar concentration of the anionic surfactants (I) used in the present invention is high when compared with nonionic surfactants, the anionic surfactants (I) can be readily removed by dialysis or electrodialysis.

(e) The anionic surfactants (I) usable in the present invention not only solubilize biomembrane proteins without denaturing, but also remarkably suppress the denaturation of a biomembrane protein in a medium utilized in the present invention.

EXAMPLE

The present invention will now be further illustrated by, but is by no means limited to, the following Examples, Reference Examples, and Comparative Examples, in which $(Na^+, K^+)$ ATPase of canine renal outer medulla was separated and purified.

(1) The ATPase activity after the separation and purification was determined as follows.

An appropriate amount of phospholipids derived from soybean is added to a 30 mM imidazol/30 mM glycidyl glycine buffer solution (pH 7.2, 20° C.) containing 4 mM ATP, 100 mM NaCl, 25 mM KCl, 3.9 mM $MgCl_2$, and 0.2 mM EDTA. The mixture was treated at a temperature of 37° C. for 2.5 to 4 minutes. Then, a concentrated aqueous SDS solution was added to terminate the reaction. Thereafter, the formation or non-formation of inorganic phosphoric acid was determined according to the methods of Hegyvary et al (see Anal. Biochem., 94, 397–401(1979)).

(2) The degree of the separation and purification of biomembrane protein was evaluated as follows.

After the polyacrylamide gel electrophoresis according to the present invention was completed, the gel was taken out and, then, a conventional SDS-polyacrylamide gel electrophoresis of it was performed using a slab type two-dimensional electrophoresis device. It is reported by Y. Hayashi et al., (B.B.A., 748, 153–167(1983)) that $(Na^+, K^+)$ ATPase comprises two kinds of subunits, $\alpha$ and $\beta$, each having different molecular weights, and that a few or several subunits are gathered to form oligomers, such as $\alpha\beta$, $(\alpha\beta)_2$ and $(\alpha\beta)_n$ type. When pure $(Na^+, K^+)$ ATPase is subjected to SDS-polyacrylamide gel electrophoresis, only two bands corresponding to $\alpha$- and $\beta$-subunits are obtained and no other bands are observed. Accordingly, the purity of $(Na^+, K^+)$ ATPase can be evaluated by the presence or absence of the third band after the electrophoresis.

REFERENCE EXAMPLE

Polyacrylamide gel electrophoresis of $(Na^+, K^+)$ ATPase purified by a Jorgensen method disclosed in B.B.A., 356, 36–52(1974) was carried out at room temperature in the presence of $C_{12}H_{25}O(CH_2CH_2O)_8SO_3Na$.

The compositions of gel and buffer solutions used in the one dimensional and two-dimensional polyacrylamide gel electrophoresis were as shown in Tables 1 and 2, respectively.

TABLE 1

| Gel Composition | |
|---|---|
| Acrylamide | 5 wt. % |
| N,N'—methylenebisacrylamide | 2.7 wt. % (based on the amount of the acrylamide) |
| Ammonium persulfate | 0.07 wt. % |
| N,N,N',N'—tetramethylene diamine | 0.15 wt. % |
| Phosphate buffer (pH = 7) | 100 mM |
| Surfactant | 0.1 wt. % |
| Water | Balance |

TABLE 2

| Buffer Composition | |
|---|---|
| Phosphate buffer (pH = 7) | 100 mM |
| Surfactant | 0.1 wt. % |
| Water | Balance |

The gel electrophoresis was carried out according to a conventional SDS-polyacrylamide gel electrophoresis method disclosed in, for example, J. V. Maizel, Jr., "Methods in Virology", Academic Press. (1971), p179 and Toshio Takagi and Jun Miyake "Shin Jikken Kagaku Kouza Vol. 20, Seibutsu Kagaku I (Edited by Nippon Kagaku Kai)" Maruzen (1978), p109, except that no SS linkage dissociating agents were used and that SDS was substituted for the anionic surfactant, i.e., $C_{12}H_{25}O$—$(CH_2CH_2O)_8SO_3Na$.

In summary, the polyacrylamide gel electrophoresis was carried out as follows:

Polyacrylamide gel electrophoresis was carried out in gels (0.5×8.0 cm) having a composition illustrated in Table 1. Bromophenol Blue was used as a marker dye. About 20 $\mu l$ of a sample solution containing about 10 $\mu g$ of $(Na^+, K^+)$ ATPase were applied per gel. Electrophoresis was performed at 10 mA per gel for 3 hr. Protein bands in the gel were stained by Amido Black, followed by destaining in acetic acid solution in order to remove excess stain from the background.

As a result of the above mentioned electrophoresis, two clear bands were obtained. After migrating protein bands out of the gel, of course the gel is another one performed at the same time, the presence or absence of ATPase activity was determined. The result was positive. In addition, after removing the gel from the tube, the gel was subjected to a conventional SDS-polyacrylamide gel electrophoresis using a slab-type two dimensional electrophoresis apparatus. As a result, two spots corresponding to $\alpha$- or $\beta$-subunit, respectively, were obtained from two bands. No other spots were observed. It should be noted, however, that a difference between the mobility of the bands of the one-dimensional and two-dimensional gel electrophoresis was observed. It is believed that this exhibits the difference between the effect of the use of the anionic surfactant according to the present invention and SDS on the hydrodynamic volume of the α- and β-subunits. That is, the two bands obtained by the polyacrylamide gel electrophoresis according to the present invention are α- and β-subunits respectively and these subunits can retain the enzymatic activity by the reconstitution. That is, according to the present invention, the desired biomembrane protein can be separated and purified from a biomembrane, with a high purity and without impairing its biological function.

EXAMPLE 1

Microsome obtained from canine kidney was mixed with a 1% by weight aqueous solution of $C_{12}H_{25}O(CH_2CH_2O)_8SO_3Na$. The mixture was subjected to ultrasound treatment and, then, was centrifugally separated. The supernatant was collected. The separation and purification of this supernatant was carried out under the same conditions as in the Reference Example.

The gel portions exhibiting mobility corresponding to that of the two bands obtained in the Reference Example were cut off and the membrane protein contained in these portions was recovered. The ATPase activity of the recovered protein was positive. When the degree of the separation and purification was confirmed in SDS-polyacrylamide gel electrophoresis using a slab-type two-dimensional gel electrophoresis apparatus, clear spots were observed corresponding to α- and β-subunits from the two bands and no other spots were observed. Thus, the degree of separation and purification of the membrane protein was extremely high. Furthermore, the difference in the mobility of each band between in the one-dimensional gel electrophoresis and two-dimensional gel electrophoresis was observed.

EXAMPLE 2

The gel electrophoresis separation and purification of the biomembrane protein was carried out in the same manner as in Example 1, except that the anionic surfactant of Example 1 was replaced by sodium polyoxyethylene (ave, 7 mol) laurylether sulfate. However, since the migration velocity of $(Na^+, K^+)$ ATPase in the polyacrylamide gel electrophoresis according to the present invention is different depending upon the anionic surfactant used, the preliminary test set forth in the Reference Example was carried out by substituting the above-mentioned surfactant for the surfactant in the Reference Example, whereby the migrated position of the desired membrane protein was previously determined.

As a result, the ATPase activity was positive and the purity was very high.

EXAMPLE 3

The gel electrophoresis separation and purification of the biomembrane protein was carried out in the same manner as in Examples 1 and 2, except that sodium polyoxyethylene (ave, 10 mol) nonylphenyl ether sulfate was used as the anionic surfactant.

The ATPase activity was positive and the purity was extremely high.

COMPARATIVE EXAMPLE 1

The gel electrophoresis separation and purification of the Reference Example was carried out by using, as a surfactant, SDS. As a result, two clear bands were obtained. The two clear band portions were cut off, and then the two band portions were reconstituted. When the ATPase activity was determined the result was negative. Furthermore, when the purity was determined by using a slab-type two dimensional gel electrophoresis method, one of the two clear bands having the larger mobility yielded a single spot also having a large mobility in the two-dimensional electrophoresis. On the other hand, the other clear band having a relatively small mobility also yielded a single spot having a relatively small mobility. There was no substantial difference in the mobility of each band between the two dimensional electrophoresis and the first one-dimensional electrophoresis.

As is clear from the above-mentioned results, when SDS is used, the hydrodynamic volumes of the α- and β-subunits of $(Na^+, K^+)$ ATPase were changed so that recovery of the enzymatic activity was impossible.

EXAMPLE 4

The gel electrophoresis separation and purification of the biomembrane protein was carried out in the same manner as in Example 3, except that sodium poly(oxypropylene (ave. 2 mol)-oxyethylene (ave. 3 mol.) lauryl ether sulfate was used as the anionic surfactant.

As a result, the ATPase activity was positive and the purity was extremely high.

EXAMPLE 5

Microsome fractionatedly obtained from canine kidney was mixed with a 1% by weight aqueous solution of $C_{12}H_{25}O(CH_2CH_2O)_8SO_3Na$. The mixture was subjected to ultrasound treatment and, then, was centrifugally separated. The supernatant was collected. The separation and purification of this supernatant was carried out under the same conditions as in the Reference Example, except that the gel was cooled with water having a temperature of 0° C. during the electrophoresis.

As a result, one clear band was observed. The portion was recovered from the gel, in which electrophoresis was performed in parallel and not stained, by cutting off the gel portion corresponding to the clear band. The ATPase activity of this was positive. In addition, the degree of separation and purification was determined by a conventional SDS-polyacrylamide gel electrophoresis using a slab-type two-dimensional electrophoresis apparatus. As a result, spots corresponding to α- and β-subunits, respectively, were obtained. No other spots were observed.

Accordingly, it is clear that, when the gel electrophoresis was carried out around 0° C., the recovery of the enzymatic activity is advantageously effected by the reconstitution since the splitting of the protein into α- and β-subunits was suppressed.

EXAMPLE 6

The gel electrophoresis separation and purification of the biomembrane protein was carried out in the same manner as in Example 5, except that sodium polyoxyethylene (ave. 7 mol) lauryl ether sulfate was used as the anionic surfactant.

As a result, the ATPase activity was positive and the purity was extremely high.

EXAMPLE 7

The gel electrophoresis separation and purification of the biomembrane protein was carried out in the same manner as in Example 5, except that sodium poly(oxypropylene (ave. 2 mol)-oxyethylene (ave. 5 mol) lauryl ether sulfate was used as the anionic surfactant.

As a result, the ATPase activity was positive and the purity was extremely high.

We claim:

1. A method for separating and purifying a biomembrane protein which is solubilized from a biomembrane into an aqueous solution containing at least one anionic surfactant by subjecting the biomembrane protein to gel electrophoresis in which at least one anionic surfactant is incorporated into a gel comprising a supporting medium, said anionic surfactant having the general formula (I):

$$RO{-}XO)_m\,(YO)_n\,SO_3M \qquad (I)$$

wherein R represents an alkyl group having 6 to 22 carbon atoms or an alkylphenyl group having 6 to 22 carbon atoms, X and Y independently represent a hydrocarbon residue having 1 to 4 carbon atoms, m and n independently represent a number of from zero to 40 provided that $m+n$ is 4 to 40, and M represents an alkali metal, an alkaline earth metal, an amine, or ammonium.

2. A method as claimed in claim 1, wherein said anionic surfactant is sodium polyoxyethylene lauryl ether sulfate, having an average molecule unit number of oxyethylene of 8 sodium octapolyoxyethylene dodecyl ether sulfate, sodium polyoxyethylene branched nonylphenyl ether sulfate having an average molecule unit number of oxyethylene of 6.9, ammonium polyoxyethylene lauryl ether sulfate having an average molecule unit number of oxyethylene of 7, triethanolammonium polyoxyethylene dodecyl ether sulfate having an average molecular unit number of oxyethylene of 6, sodium poly(oxypropylene-oxyethylene) lauryl ether sulfate having average molecular unit numbers of oxypropylene and oxyethylene of 2 and 5, respectively.

3. A method as claimed in claim 1, wherein a supporting medium in the gel electrophoresis is at least one member selected from the group consisting of cellulose acetate, sephadex, vinyl chloride-vinyl acetate copolymer, polyvinyl chloride, starch powder, starch gel, agarose gel, and polyacrylamide gel.

4. A method as claimed in claim 1, wherein the concentration of the anionic surfactant in the gel is 0.01% to 1% by weight.

5. A method as claimed in claim 1, wherein an aqueous solution of the biomembrane protein contains 0.1% to 5% by weight of the anionic surfactant.

* * * * *